United States Patent
Morozov et al.

(10) Patent No.: US 10,962,696 B2
(45) Date of Patent: Mar. 30, 2021

(54) COATABLE GREY POLARIZER

(71) Applicant: LIGHT POLYMERS HOLDING, George Town (KY)

(72) Inventors: Evgeny Morozov, Burlingame, CA (US); Chih-Hao Huang, New Taipei (TW); Valeriy Kuzmin, Castro Valley, CA (US)

(73) Assignee: Light Polymers Holding, Grand Cayman (KY)

( * ) Notice: Subject to any disclaimer, the term of this patent is extended or adjusted under 35 U.S.C. 154(b) by 205 days.

(21) Appl. No.: 16/259,438

(22) Filed: Jan. 28, 2019

(65) Prior Publication Data

US 2019/0235144 A1 Aug. 1, 2019

Related U.S. Application Data (60) Provisional application No. 62/624,407, filed on Jan. 31, 2018, provisional application No. 62/652,591, filed on Apr. 4, 2018.

(51) Int. Cl.
*G02B 5/30* (2006.01)
*H01L 51/52* (2006.01)
(Continued)

(52) U.S. Cl.
CPC ......... *G02B 5/3016* (2013.01); *C07D 487/22* (2013.01); *C09K 19/60* (2013.01);
(Continued)

(58) Field of Classification Search
CPC . C07D 489/00; C07D 487/22; H01L 51/5281; H01L 27/156; G02B 5/3016;
(Continued)

(56) References Cited

U.S. PATENT DOCUMENTS 3,208,814 A 9/1965 Sievenpiper et al.
4,179,395 A * 12/1979 Cole, Jr. .................. C09B 35/35
                                                              252/299.1
(Continued)

FOREIGN PATENT DOCUMENTS

EP          0489951     6/1992
JP          06235917    8/1994
(Continued)

OTHER PUBLICATIONS

Gribkova "Chemical synthesis of polyaniline in the presence of poly(amidosulfonic acids) with different rigidity of the polymer chain," Apr. 2011, *Polymer* 52(12):2474-2484.
(Continued)

*Primary Examiner* — William R Alexander
(74) *Attorney, Agent, or Firm* — Mueting Raasch Group (57) ABSTRACT

A linear polarizer may be formed a blue dichroic dye compound, having a maximum dichroic ratio $Kd \leq 12$ in an entire visible wavelength range, and a red dichroic dye compound, having a maximum dichroic ratio $Kd \leq 16$ in the entire visible wavelength range. The linear polarizer has a dichroic ratio $Kd \geq 18$ and a thickness of less than or equal to 2 micrometers. The linear polarizer may form an achromatic polarizer.

20 Claims, 4 Drawing Sheets

(51) Int. Cl.
*C09K 19/60* (2006.01)
*C07D 487/22* (2006.01)
C09B 5/34 (2006.01)
H01L 27/15 (2006.01)
C09B 5/32 (2006.01)

(52) U.S. Cl.
CPC .......... *C09K 19/603* (2013.01); *C09K 19/606* (2013.01); *G02B 5/3033* (2013.01); *H01L 51/5281* (2013.01); *C09B 5/32* (2013.01); *C09B 5/34* (2013.01); *H01L 27/156* (2013.01)

(58) Field of Classification Search
CPC ........ G02B 5/3033; G02B 5/30; C09K 19/60; C09K 19/603; C09K 19/606; C09B 5/32; C09B 5/34
USPC .................................................... 359/487.02
See application file for complete search history.

(56) References Cited

U.S. PATENT DOCUMENTS

| | | |
|---|---|---|
| 4,278,578 A | 7/1981 | Carpenter |
| 4,605,698 A | 8/1986 | Briden |
| 5,067,797 A | 11/1991 | Yokokura et al. |
| 5,739,296 A | 4/1998 | Gvon et al. |
| 5,863,113 A | 1/1999 | Oe et al. |
| 6,002,829 A | 12/1999 | Winston et al. |
| 6,045,894 A | 4/2000 | Jonza et al. |
| 6,049,428 A | 4/2000 | Khan et al. |
| 6,144,424 A | 11/2000 | Okuda et al. |
| 6,174,394 B1 | 1/2001 | Gvon et al. |
| 6,322,236 B1 | 11/2001 | Campbell et al. |
| 6,399,166 B1 | 6/2002 | Khan et al. |
| 6,481,864 B2 | 11/2002 | Hosseini et al. |
| 6,563,640 B1 | 5/2003 | Ignatov et al. |
| 6,583,284 B1 | 6/2003 | Sidorenko et al. |
| 6,619,553 B1 | 9/2003 | Bobrov et al. |
| 6,734,936 B1 | 5/2004 | Schadt et al. |
| 6,841,320 B2 | 1/2005 | Lazarev et al. |
| 6,846,522 B1 | 1/2005 | Bobrov et al. |
| 6,847,420 B2 | 1/2005 | Lazarev et al. |
| 6,848,897 B2 | 2/2005 | Lazarev et al. |
| 6,876,806 B2 | 4/2005 | Lazarev et al. |
| 6,913,783 B2 | 7/2005 | Lazarev et al. |
| 6,942,925 B1 | 9/2005 | Lazarev et al. |
| 6,962,734 B2 | 11/2005 | Nazarov et al. |
| 7,015,990 B2 | 3/2006 | Yeh et al. |
| 7,025,900 B2 | 4/2006 | Sidorenko et al. |
| 7,026,019 B2 | 4/2006 | Dutova et al. |
| 7,031,053 B2 | 4/2006 | Bobrov et al. |
| 7,042,612 B2 | 5/2006 | Lazarev et al. |
| 7,045,177 B2 | 5/2006 | Dutova et al. |
| 7,053,970 B2 | 5/2006 | Lazarev |
| 7,084,939 B2 | 8/2006 | Paukshto et al. |
| 7,092,163 B2 | 8/2006 | Bastawros et al. |
| 7,106,398 B2 | 9/2006 | Bobrov |
| 7,108,749 B2 | 9/2006 | Bobrov |
| 7,110,177 B2 | 9/2006 | Sugino et al. |
| 7,113,337 B2 | 9/2006 | Lazarev et al. |
| 7,132,138 B2 | 11/2006 | Lazarev |
| 7,144,608 B2 * | 12/2006 | Paukshto ........... C09K 19/3452 428/1.31 |
| 7,160,485 B2 | 1/2007 | Nazarov et al. |
| 7,166,161 B2 | 1/2007 | Lazarev et al. |
| 7,190,416 B2 | 3/2007 | Paukshto et al. |
| 7,204,938 B2 | 4/2007 | Lazarev |
| 7,211,824 B2 | 5/2007 | Lazarev |
| 7,267,849 B2 | 9/2007 | Lazarev et al. |
| 7,271,863 B2 | 9/2007 | Paukshto et al. |
| 7,291,223 B2 | 11/2007 | Lazarev |
| 7,297,209 B2 | 11/2007 | Lazarev et al. |
| 7,315,338 B2 | 1/2008 | Yeh et al. |
| 7,317,499 B2 | 1/2008 | Paukshto et al. |
| 7,324,181 B2 | 1/2008 | Lazarev et al. |
| 7,405,787 B2 | 7/2008 | Paukshto et al. |
| 7,450,194 B2 | 11/2008 | Lazarev |
| 7,456,915 B2 | 11/2008 | Lazarev et al. |
| 7,479,311 B2 | 1/2009 | Bobrov |
| 7,480,021 B2 | 1/2009 | Rao et al. |
| 7,554,636 B2 | 6/2009 | Nakatsugawa |
| 7,557,876 B2 | 7/2009 | Lazarev et al. |
| 7,651,738 B2 | 1/2010 | Grodsky et al. |
| 7,660,047 B1 | 2/2010 | Travis et al. |
| 7,733,443 B2 | 6/2010 | Lazarev et al. |
| 7,850,868 B2 | 12/2010 | Matsuda et al. |
| 7,888,505 B2 | 2/2011 | Doutova et al. |
| 7,889,297 B2 | 2/2011 | Palto |
| 7,911,557 B2 | 3/2011 | Lazarev et al. |
| 7,969,531 B1 | 6/2011 | Li et al. |
| 8,081,270 B2 | 12/2011 | Lazarev |
| 8,142,863 B2 | 3/2012 | Palto |
| 8,168,082 B2 | 5/2012 | Matsuda et al. |
| 8,189,165 B2 | 5/2012 | Umemoto et al. |
| 8,257,802 B2 | 9/2012 | Inoue et al. |
| 8,268,937 B2 | 9/2012 | Bos et al. |
| 8,305,350 B2 | 11/2012 | Chang |
| 8,404,066 B2 | 3/2013 | Goto et al. |
| 8,416,376 B2 | 4/2013 | Palto |
| 8,512,824 B2 | 8/2013 | Kasianova et al. |
| 8,551,357 B2 | 10/2013 | Miyazaki et al. |
| 10,023,123 B2 * | 7/2018 | Takada ................ B60R 1/083 |
| 2003/0179363 A1 | 9/2003 | Wang |
| 2004/0146663 A1 * | 7/2004 | Paukshto .......... G02F 1/133528 428/1.31 |
| 2007/0064417 A1 | 3/2007 | Hatanaka et al. |
| 2007/0110378 A1 | 5/2007 | Zarian |
| 2007/0159580 A1 * | 7/2007 | Yoshioka ............. G02B 5/3008 349/117 |
| 2007/0279934 A1 | 12/2007 | Kim et al. |
| 2007/0285599 A1 | 12/2007 | Oxude |
| 2008/0042154 A1 | 2/2008 | Wano |
| 2008/0074595 A1 | 3/2008 | Nakatsugawa |
| 2008/0252974 A1 * | 10/2008 | Futamura .......... G02F 1/133528 359/487.06 |
| 2008/0278673 A1 * | 11/2008 | Yoshioka .......... G02F 1/133528 349/194 |
| 2008/0298067 A1 | 12/2008 | Chu |
| 2008/0304283 A1 | 12/2008 | Parker et al. |
| 2009/0269591 A1 | 10/2009 | Kasianova et al. |
| 2010/0039705 A1 | 2/2010 | Doutova et al. |
| 2010/0085521 A1 | 4/2010 | Kasianova et al. |
| 2010/0149471 A1 | 6/2010 | Palto |
| 2010/0190015 A1 | 7/2010 | Kasianova |
| 2010/0215954 A1 | 8/2010 | Kuzmin et al. |
| 2011/0149206 A1 | 6/2011 | Lazarev |
| 2011/0149393 A1 | 6/2011 | Nokel et al. |
| 2011/0182084 A1 | 7/2011 | Tomlinson et al. |
| 2011/0255305 A1 | 10/2011 | Chen et al. |
| 2012/0013982 A1 | 1/2012 | Kharatiyan |
| 2012/0081784 A1 | 4/2012 | Lazarev |
| 2012/0099052 A1 | 4/2012 | Lazarev |
| 2012/0113380 A1 | 5/2012 | Geivandov et al. |
| 2012/0113678 A1 | 5/2012 | Cornelissen et al. |
| 2012/0113680 A1 | 5/2012 | Nakai et al. |
| 2012/0244330 A1 | 9/2012 | Sun |
| 2013/0003178 A1 | 1/2013 | Lazarev |
| 2013/0011642 A1 | 1/2013 | Sun |
| 2013/0070480 A1 | 3/2013 | Griffin et al. |
| 2013/0251947 A1 | 9/2013 | Lazarev |
| 2014/0133177 A1 | 5/2014 | Miller et al. |
| 2014/0140091 A1 | 5/2014 | Vasylyev |
| 2014/0186637 A1 | 7/2014 | Kasianova et al. |
| 2014/0320961 A1 | 10/2014 | Lazarev |
| 2014/0322452 A1 | 10/2014 | Kasyanova et al. |
| 2014/0350214 A1 | 11/2014 | Kharatiyan |
| 2015/0086799 A1 | 3/2015 | Kasyanova et al. |
| 2015/0123911 A1 | 5/2015 | Poliakov et al. |
| 2015/0266999 A1 | 9/2015 | Kuzmin et al. |
| 2016/0200255 A1 * | 7/2016 | Takada ................ B60R 1/084 359/488.01 |

(56) References Cited

U.S. PATENT DOCUMENTS

2017/0184769 A1\* 6/2017 Kim .................... G02B 5/3083
2019/0391433 A1\* 12/2019 Hashimoto ............... B32B 7/02

FOREIGN PATENT DOCUMENTS

| JP | 2010-091984 A | 4/2010 |
| WO | WO 2010-064194 A1 | 6/2010 |
| WO | WO 2012-007923 A1 | 1/2012 |
| WO | WO 2013-119922 A1 | 8/2013 |
| WO | WO 2014/174381 | 10/2014 |

OTHER PUBLICATIONS

Kasianova, "New Transparent Birefringent Material for Interference Polarizer Fabrication" 2006 *XV International Symposium Advanced Display Technologies* (ADT '06), Moscow, Russia, 1-6.

Konoshchuk, "Physicochemical Properties of Chemically and Mechanochemically Prepared Interpolymer Complexes of Poly(3,4-Ethylenedioxythiophene) with Polyamidosulfonate Dopants," Jan. 2014, *Theoretical and Experimental Chemistry* 50(1): 21-28 (Russian Original, Jan. 2014).

Koo et al., "Preparation and humidity-sensitive properties of novel photocurable sulfonated polyimides," *Macromolecular Research*, Dec. 1, 2012, 20(12):1226-1233.

Li, "Design Optimization of Reflective Polarizers for LCD Backlight Recycling" Aug. 2009 *J Display Tech.*, 56(8): 335-340.

\* cited by examiner

COATABLE GREY POLARIZER

BACKGROUND

Light consists of electromagnetic fields that oscillate in a direction perpendicular to the direction of propagation. Unpolarized light is the most general case of light polarization, and linear, elliptical, and circular polarizations are specific cases. Linearly polarized light is the case where electromagnetic fields oscillate in a plane, and this plane defines the polarization plane. One can convert polarization from linear polarization to circular or elliptical polarization. Polarized light may be used in a variety of optical devices in general and display in devices in particular.

A polarizer is an optical filter that passes light of a specific polarization and blocks waves of other polarizations. It can convert a beam of light of undefined or mixed polarization into a beam with well-defined polarization, polarized light. The common types of polarizers are linear polarizers and circular polarizers. Polarizers are used in many optical techniques and instruments, and polarizing filters find applications in photography and liquid crystal display technology.

Current polarizer technology utilizes a polarizing film formed of a polyvinyl alcohol type resin layer having a dichroic material impregnated therein. Such known technologies include a method wherein a polyvinyl alcohol type resin layer is formed by coating and drying a solution of polyvinyl alcohol type resin on a resin substrate and then subjecting this resin layer to a stretching process, and then subjecting the stretched resin substrate to a dyeing process to form a polarizing film having a dichroic material impregnated therein in a molecularly oriented state. Alternatively, a method includes forming a polyvinyl alcohol type resin layer and applying a dichroic material therein, and then stretching the dyed resin layer to form a polarizing film having the dichroic material impregnated therein in a molecularly oriented state.

A liquid-crystal display element can have a polarizing film (described above) laminated on each of a front and back surface of a liquid-crystal cell. The polarizing film typically has a thickness of at least 20 micrometers. These polarizing films typically include additional barrier layers to maintain the dimensional stability of the polarizing film but add thickness to the polarizing film element.

In recent years, OLED (organic light-emitting diode) technology has come into wide use in Smartphones and TVs. Each pixel in an OLED display has a cathode and an anode. Since the cathode is metallic, ambient light that enters the OLED display and is incident on a cathode gets reflected. Light that gets past the cathode may be reflected from a reflection film underneath the TFT (thin-film transistor) substrate. A circular polarizer is inserted in the OLED display in order to address the problem of contrast degradation due to ambient light reflection. The circular polarizer consists of a linear polarizer and a quarter-wave plate (QWP). Unpolarized ambient light is polarized by the linear polarizer; the linearly polarized light is converted to circularly polarized light upon passing through the QWP. The handedness of the circularly polarized light is switched upon reflection from the metallic layer, so most of the reflected light does not pass through the linear polarizer.

For both LCDs and OLEDs, there is an interest in realizing foldable displays for mobile applications. In order to make this possible, it is important to provide polarizers that are thinner or polarizers that can be directly coated on the display substrate. Therefore, improvements in polarizer technology are desired.

SUMMARY

The present disclosure relates to a coatable grey polarizer. The coatable grey polarizer may be formed with a composition that includes two or more dichroic dye compounds that exhibit a dichroic ratio that is greater than the dichroic ratio of either individual dichroic dye compound forming the composition. The coatable grey polarizer may form an achromatic polarizer.

In one aspect, a linear polarizer may be formed a blue dichroic dye compound, having a maximum dichroic ratio $Kd \leq 12$ in an entire visible wavelength range, and a red dichroic dye compound, having a maximum dichroic ratio $Kd \leq 16$ in the entire visible wavelength range. The linear polarizer has a dichroic ratio $Kd \geq 18$ and a thickness of less than or equal to 2 micrometers. The linear polarizer may form an achromatic polarizer.

The blue dichroic dye compound may have its maximum visible light absorption in a wavelength range 600 nm-700 nm and a maximum dichroic ratio $Kd \leq 12$ in an entire visible wavelength range (such as at 550 nm). The red dichroic dye compound may have its maximum visible light absorption in a wavelength range 430 nm-520 nm and a maximum dichroic ratio $Kd \leq 16$ in the entire visible wavelength range (such as at 550 nm). The linear polarizer has a dichroic ratio at 550 nm, and a thickness of the linear polarizer is less than or equal to 2 micrometers.

In another aspect, a linear polarizer film includes a substrate and a linear polarizer, described herein, overlying the substrate.

In another aspect, a circular polarizer includes a retarder, configured as an achromatic quarter-wave plate, and a linear polarizer, described herein, overlying the retarder such that the retarder and a first major surface of the linear polarizer are facing toward each other.

In another aspect, a light emissive display module includes a substrate, an array of light emissive elements overlying the substrate, and a circular polarizer, described herein, overlying the array of light emissive elements.

In a further aspect, a lyotropic liquid crystal formulation includes a blue lyotropic liquid crystal, a red lyotropic liquid crystal, and a violet lyotropic liquid crystal. The blue lyotropic liquid crystal includes a blue compound of structure B:

(Structure B)

wherein: X is a SO$_3$H (sulfonic) group or a salt thereof, and 1≤m≤4; Z is a Cl (chloro) group, and 0≤p≤2; and m+p≤4. The red lyotropic liquid crystal includes a red compound of structure R:

(Structure R)

or a trans-isomer of structure R, wherein, X is a SO$_3$H (sulfonic) group or a salt thereof. The violet lyotropic liquid crystal includes a violet compound having a structure Va:

(Structure Va)

or a cis-isomer of structure Va, wherein: X is a SO$_3$H (sulfonic) group or a salt thereof, and 1≤m≤4; Y is a S(=O)$_2$ (sulfone) group, and 0≤n≤2; Z is a OH (hydroxy) group, and 0≤p≤4; R is an O (oxo) group, and 0≤q≤4; and m+p+q≤6. This lyotropic liquid crystal formulation may have the blue:violet:red compounds present in a solids weight ratio of 100:35-45:40-50.

In a further aspect, a lyotropic liquid crystal formulation includes a blue lyotropic liquid crystal, a red lyotropic liquid crystal, and a yellow lyotropic liquid crystal. The blue lyotropic liquid crystal includes a blue compound of structure B:

(Structure B)

wherein: X is a SO$_3$H (sulfonic) group or a salt thereof, and 1≤m≤4; Z is a Cl (chloro) group, and 0≤p≤2; and m+p≤4. The red lyotropic liquid crystal includes a red compound of structure R:

(Structure R)

or a trans-isomer of structure R, wherein, X is a SO$_3$H (sulfonic) group or a salt thereof. The yellow lyotropic liquid crystal includes a yellow compound having a structure Y:

(Structure Y)

wherein: X is a SO$_3$H (sulfonic) group or a salt thereof, and 1≤m≤4; Z is a Cl (chloro) group, and 0≤p≤2; and m+p≤6.

These and various other features and advantages will be apparent from a reading of the following detailed description.

BRIEF DESCRIPTION OF THE DRAWING

The disclosure may be more completely understood in consideration of the following detailed description of various embodiments of the disclosure in connection with the accompanying drawings; in which.

DETAILED DESCRIPTION

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

In this disclosure:

"visible light" refers to light wavelengths generally from about 400 nm to about 800 nm;

"achromatic" refers to color-less

"dichroic ratio" or "Kd" refers to a ratio $\alpha_{max}/\alpha_{min}$, of an absorption coefficient $\alpha_{max}$ along a first direction within the plane of the polarizer showing the maximum absorption to an absorption coefficient $\alpha_{min}$ along a second direction within the plane of the polarizer showing the minimum absorption.

The present disclosure relates to a coatable polarizer or a lyotropic liquid crystal coatable composition or formulation that may be coated onto a substrate to form a polarizer and preferably an achromatic linear polarizer. The coatable polarizer may be referred to as a grey polarizer. The coatable grey polarizer may be formed with a composition that includes two or more dichroic dye compounds that exhibit a dichroic ratio that is greater than the dichroic ratio of either individual dichroic dye compound forming the composition. The coatable grey polarizer may form an achromatic polarizer. The linear polarizer may be formed a blue dichroic dye compound, having a dichroic ratio $Kd \leq 12$ in a visible wavelength range, and a red dichroic dye compound, having a dichroic ratio $Kd \leq 16$ in the visible wavelength range. The linear polarizer has a dichroic ratio $Kd \geq 18$ and a thickness of less than or equal to 2 micrometers. The linear polarizer may form an achromatic polarizer. The blue dichroic dye compound may have its maximum visible light absorption in a wavelength range 600 nm-700 nm and a dichroic ratio $Kd \leq 12$ in a visible wavelength range (such as at 550 nm). The red dichroic dye compound may have its maximum visible light absorption in a wavelength range 430 nm-520 nm and a dichroic ratio $Kd \leq 16$ in the visible wavelength range (such as at 550 nm). The linear polarizer has a dichroic ratio $Kd \geq 18$ at 550 nm, and a thickness of the linear polarizer is less than or equal to 2 micrometers. The coatable grey polarizer may be formed from a lyotropic liquid crystal material solution coated onto a substrate to create a layer of aligned material transmitting most visible light of a first polarization and absorbing most visible light having a second polarization (generally orthogonal to the first polarization). This coatable grey polarizer may be achromatic and appear clear, black or grey. This coatable grey polarizer may have a thickness of less than five micrometers or less than one micrometer, or less than one micrometer. The aligned material may be formed by shear coating the lyotropic liquid crystal material onto a substrate. The lyotropic liquid crystal material can be coated directly onto an optical element such as a glass substrate of a LCD panel. The optical element may be a planar surface or a curved surface. This coatable grey polarizer be utilized to form a circular polarizer, eyewear, or displays. While the present disclosure is not so limited, an appreciation of various aspects of the disclosure will be gained through a discussion of the examples provided below.

The linear polarizer or linear grey polarizer is formed from aligned coatings that are prepared from lyotropic liquid crystal solutions of dichroic dye compounds, described below. An aligned coating layer is obtained by shear coating these lyotropic liquid crystal solutions of dichroic dye compounds. The dichroic dye compounds may be combined with other chromonic mesogens or molecules, polymers or small molecules to form the optical coating layer.

Shear coating methods include slot coating, slit coating, doctor blade coating, die coating, slot-die coating, gravure coating, micro-gravure coating, curtain coating and the like. After the shear coating step, the coated solution is dried to remove the solvent (such as water) and form a polarizer or linear polarizer (optical coating layer). The optical coating layer may be stabilized by converting it to a water-insoluble layer. This conversion can be accomplished by ion exchange of mono-valent ions with di-valent or tri-valent ions.

The polarizer or linear polarizer may be coated directly onto a substrate or an optical element. The substrate or an optical element may be primed and/or corona treated to improve adhesion of the optical coating to the surface of the substrate or an optical element. The final optical coating layer or polarizer or linear polarizer has any useful thickness (dry thickness). The final optical coating or polarizer or linear polarizer may have a thickness of less than 10 micrometers, or less than 5 micrometers, or less than 3 micrometers, or less than 2 micrometers, or less than 1 micrometer, or less than 750 nm. The optical coating or polarizer or linear polarizer may have a thickness in a range from 250 nanometers to 5 micrometers, or from 500 nanometers to 2 micrometers, or from 500 nanometers to 1 micrometer, or from 500 nanometers to 1000 nanometers.

The optical coating (lyotropic liquid crystal solution of dichroic dye compounds) may be utilized to alter or modify spectral or polarization properties of light incident on the optical coating. In many embodiments, this optical coating transmits visible light. This optical coating may be achromatic. This optical coating may be formed of a mixture of dichroic dye compounds, such as two or more dichroic dye compounds, or three or more dichroic dye compounds, where each dichroic dye compound has a different structure, or color. Each dichroic dye compounds may have a different visible light absorption or transmission spectrum. A variety of different dichroic dye compounds may form a mixture that results in an achromatic optical coating (for example, an achromatic polarizer layer).

The substrate may be glass or a polymeric layer such as a polyolefin (PET or PEN), polycarbonate, or polyimide and the like. Glass substrates may form an element of a liquid crystal display panel. The glass substrate may have a reduced thickness such as about 1000 micrometers or less or 500 micrometers or less. In embodiments where the substrate is a polymer layer, the polymeric layer may be a flexible film layer that may be processed in a roll-to-roll manufacturing process.

The linear polarizer described herein may be described as an achromatic or grey polarizer. This linear polarizer may uniformly absorb light at all wavelengths of the visible light spectrum, or at all wavelengths from 500 nm to 700 nm, or at all wavelengths from 400 nm to 800 nm. Uniform absorption provides the polarizer with a grey appearance. Uniform absorption may be defined as a constant absorption ±20%, or ±15%, or ±10%, or ±5%.

Dichroic ratio (Kd) a ratio $\alpha_1/\alpha_2$, of an absorption coefficient $\alpha_1$ along a first direction within the plane of the polarizer showing the maximum absorption (minimum transmittance) to an absorption coefficient $\alpha_2$ along a second direction within the plane of the polarizer showing the minimum absorption (maximum transmittance). The dichroic ratio Kd can also be expressed as $\ln(T_1)/\ln(T_2)$. $T_1$ is the polarizer transmittance for polarization along a first direction showing minimum polarizer transmittance. $T_2$ is the polarizer transmittance for polarization along a second direction showing a maximum polarizer transmittance. In the examples described herein, the first and second directions are perpendicular or approximately perpendicular to each other. Furthermore, the second direction (maximum polarizer transmittance) is approximately parallel to the shear-coating direction and the first direction (minimum polarizer transmittance) is approximately perpendicular to the shear-coating direction. This occurs because the dichroic dye molecules described herein tend to stack along the shear-coating direction.

The linear polarizers, described herein, are formed of a mixture of two different dichroic dye compounds, three different dichroic dye compounds, or four different dichroic dye compounds. The dichroic ratio (Kd) of the linear polarizer is surprisingly larger than the individual dichroic ratio (Kd) of a shear coated layer formed from each dichroic dye compound. The dichroic ratio (Kd) of the linear polarizer may be at least 5% or greater, or 10% greater, or 15% greater, or 20% greater than the individual dichroic ratio (Kd) of the shear coated layers formed from dichroic dye compounds used to form the linear polarizer.

In some embodiments, the dichroic ratio (Kd) of the linear polarizer may be at least 18 and the individual dichroic ratio (Kd) of each dichroic dye compounds used to form the linear polarizer may be no greater than 17, or no greater than 16, or no greater than 15, or no greater than 14, or no greater than 13 or no greater than 12.

In one embodiments, the dichroic ratio (Kd) of the linear polarizer is 18 or greater and the individual dichroic ratio (Kd) of each dichroic dye compounds forming the linear polarizer is 12 or less for a blue dichroic dye compound, and 16 or less for a red dichroic dye compound.

Useful dichroic dye compounds include blue dichroic dye compounds, red dichroic dye compounds, violet dichroic dye compounds, and/or yellow dichroic dye compounds.

Blue dichroic dye compounds include compounds having a structure B:

(Structure B)

wherein:

X is a $SO_3H$ (sulfonic) group or a salt thereof, and $1 \le m \le 4$;

Z is a Cl (chloro) group, and $0 \le p \le 2$; and $m+p \le 4$. In the case that X is a salt, the cation can be: $Na^+$, $K^+$, $Cs^+$, or $NH_4^+$.

Red dichroic dye compounds include compounds having a structure R:

(Structure R)

or a trans-isomer of structure R, wherein, X is a $SO_3H$ (sulfonic) group or a salt thereof. In the case that X is a salt, the cation can be: $Na^+$, $K^+$, $Cs^+$, or $NH_4^+$.

A violet dichroic dye compound has a structure Vc:

(Structure Vc)

wherein:
X is a $SO_3H$ (sulfonic) group or a salt thereof, and $1 \le m \le 4$;
Y is a $S(=O)_2$ (sulfone) group, and $0 \le n \le 2$;
Z is a OH (hydroxy) group, and $0 \le p \le 4$;
R is an O (oxo) group, and $0 \le q \le 4$; and
$m+p+q \le 6$. In the case that X is a salt, the cation can be: $Na^+$, $K^+$, $Cs^+$, or $NH_4^+$.

Another violet dichroic dye compound has a structure Va:

(Structure Va)

or a cis-isomer of structure Va, wherein:
X is a $SO_3H$ (sulfonic) group or a salt thereof, and $1 \le m \le 4$;
Y is a $S(=O)_2$ (sulfone) group, and $0 \le n \le 2$;
Z is a OH (hydroxy) group, and $0 \le p \le 4$;
R is an O (oxo) group, and $0 \le q \le 4$; and
$m+p+q \le 6$. In the case that X is a salt, the cation can be: $Na^+$, $K^+$, $Cs^+$, or $NH_4^+$.

A yellow dichroic dye compound has a structure Y:

(Structure Y)

wherein:
X is a $SO_3H$ (sulfonic) group or a salt thereof, and $1 \le m \le 4$;
Z is a Cl (chloro) group, and $0 \le p \le 2$; and
$m+p \le 6$. In the case that X is a salt, the cation can be: $Na^+$, $K^+$, $Cs^+$, or $NH_4^+$.

Useful lyotropic liquid crystal formulations include two or more dichroic dye compounds such as the blue dichroic dye compounds, red dichroic dye compounds, violet dichroic dye compounds, and/or yellow dichroic dye compounds, as described herein.

Useful lyotropic liquid crystal formulations include the red dichroic dye compounds of structure R, the blue dichroic dye compounds of structure B, and violet dichroic dye compounds of structure Vc or Va. This lyotropic liquid crystal formulation may have the blue:violet:red compounds present in a solids weight ratio of 100:35-45:40-50.

Other useful lyotropic liquid crystal formulations include the red dichroic dye compounds of structure R, the blue dichroic dye compounds of structure B, and the yellow dichroic dye compounds of structure Y.

The dichroic dye compounds, described herein, form a lyotropic liquid crystal phase can be dissolved in a useful solvent, such as water (or aqueous solvent). The dichroic dye compounds may be present in the solution in a concentration range in which a lyotropic liquid crystal is formed. The dichroic dye compounds may be present in the solution in an amount from about 1% wt to about 40% wt or from about 2% wt to about 25% wt or from about 5% wt to about 18% wt. or about 12% wt.

The dichroic dye compounds may form a lyotropic liquid crystal solution that may be shear-coated onto a substrate and dried to form the grey linear polarizer described herein. After the shear coating step, the coated solution is dried to remove the solvent (such as water) and form a polarizer or linear polarizer (optical coating layer). The optical coating layer may be stabilized by converting it to a water-insoluble layer. This conversion can be accomplished by ion exchange of mono-valent ions with di-valent or tri-valent ions. After the ion exchange, at least some of the dichroic dyes would contain cations selected from the following: $Sr^{2+}$, $Mg^{2+}$, $Ba^{2+}$, $Al^{3+}$, $La^{3+}$, $Ce^{3+}$, $Fe^{3+}$, $Cr^{3+}$, $Mn^{2+}$, $Cu^{2+}$, $Zn^{2+}$, $Pb^{2+}$, $Ca^{2+}$, $Ni^{2+}$, $Co^{2+}$, or $Sn^{2+}$.

Figure 1:
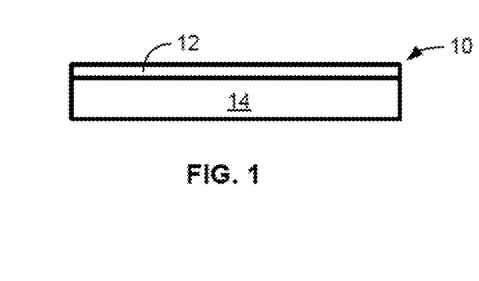
FIG. 1 is schematic diagram of an illustrative polarizing article.

FIG. 1 is schematic diagram of an illustrative polarizing article 10. The polarizing article 10 includes a substrate 14 and a coatable polarizer layer 12 disposed on the substrate 14. The substrate 14 may be any optical element and may be light transmissive. The coatable polarizer layer 12 may be coated directly onto the substrate 14 or the substrate 14 may first be primed and/or corona treated and then the coatable polarizer layer 12 is coated directly onto the primed and/or corona treated substrate 14. The coatable polarizer layer 12 may be coated onto a curved substrate 14 such as a curved display panel or a lens (for glasses or sunglasses, for example).

The substrate 14 may be glass or a polymer layer such as a polyolefin (polyethylene terephthalate (PET) or polyethylene naphthalate (PEN)), polycarbonate (PC), polyimide (PI), triacetylcellulose (TAC), cyclic olefin polymer (COP), optically clear adhesive (OCA) film, antireflection (AR) film, and the like. Glass substrates may form an element of a liquid crystal display panel or an OLED display panel. The glass substrate may have a reduced thickness such as a 1000 micrometers or less or 500 micrometers or less. In embodiments where the substrate 14 is a polymer layer, the polymer layer may be a flexible film layer that may be processed in a roll-to-roll manufacturing process.

Figure 2:
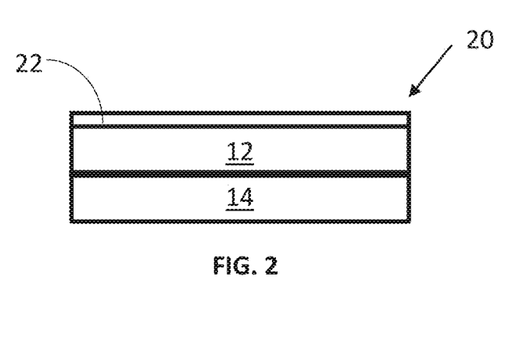
FIG. 2 is a schematic diagram of another illustrative polarizing article.

FIG. 2 is a schematic diagram of another illustrative polarizing article 20. The polarizing article 20 includes a substrate 14 and a coatable polarizer layer 12 disposed on the substrate 14 as described above. The polarizing article 20 further includes an optical element 22 disposed on the polarizer layer 12. The polarizer layer 12 separates the substrate 14 from the optical element 22. The additional optical element 22 may be a barrier layer, a hard coat layer, a release layer, an anti-reflection layer, an optically clear adhesive layer (or pressure sensitive layer), retarder (such as a quarter wave plate), and the like.

Figure 14:
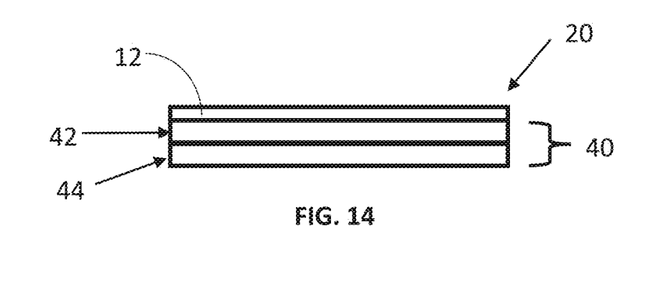
FIG. 14 is a schematic diagram of yet another illustrative polarizing article, coated on an OCA film.

In some embodiments, the coatable polymer polarizer layer 12 may be coated on an adhesive layer such as an OCA film. FIG. 14 shows a polarizing article 20 including a coatable polarizer layer 12 disposed on an OCA film 40. The OCA film includes an adhesive layer 42 and a release liner 44. The coatable polarizer layer 12 has been coated onto the adhesive layer 42. After formation of the polarizer layer 12, a release liner can be removed from the OCA film and the polarizer coating 12 can be transferred to and adhered to an optical element, display (e.g., an OLED display panel) or substrate with the adhesive layer 42 in between.

Figure 15:
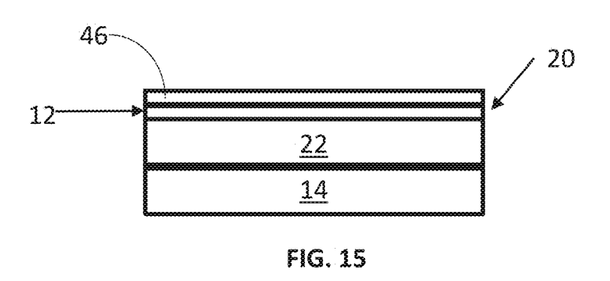
FIG. 15 is a schematic diagram of an illustrative circular polarizer.

In some embodiments, the polarizing article 20 is a circular polarizer. As shown in FIG. 15, the circular polarizer 20 includes a retarder 22, configured as an achromatic quarter-wave plate, and a linear polarizer 12, as described herein, overlying the retarder 22 such that the retarder 22 and a first major surface of the linear polarizer 12 are facing toward each other. The circular polarizer 20 may additionally include an anti-reflection coating or anti-reflection film 46 overlying the linear polarizer 12 such that the anti-reflection film or coating 46 and the second major surface of the linear polarizer are facing each other. Light initially passing through the anti-reflection coating 46 passes through the linear polarizer 12 before reaching the retarder 22.

Figure 16:
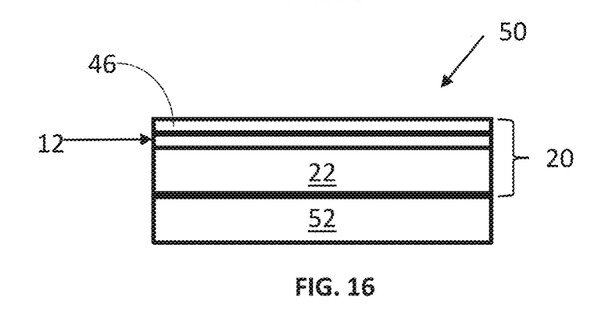
FIG. 16 is a schematic diagram of an illustrative OLED (organic light-emitting diode) display module.

FIG. 16 is a schematic illustration of an OLED display 50, which includes an OLED display panel 52 and a circular polarizer 20 described herein. For simplicity, details of the OLED display panel 52, such as TFT array, anode electrodes, cathode electrodes, organic light-emissive elements, and OLED drive circuitry have been omitted. In this Example, the circular polarizer 20 includes a QWP 22, a linear polarizer 12 overlying the QWP 22, and an anti-reflection coating or anti-reflection film 46 overlying the linear polarizer 12. The circular polarizer 20 overlies the OLED display panel 52 and is oriented relative to the OLED display panel 52 such that light emitted by the OLED display panel first passes through the QWP 22, second through the linear polarizer 12, and third through the anti-reflection coating or film 46. In other words, the circular polarizer 20 and OLED display panel 52 are oriented to each other such that the QWP 22 is closer than linear polarizer 12 to the OLED display panel 52. The circular polarizer 20 blocks most of the ambient light reflected from metallic layers in the OLED display panel 52. In this Example, the Fresnel reflection of ambient light at the interface between the linear polarizer and the ambient (e.g., air) is reduced by the presence of the anti-reflection coating or film 46.

Figure 3:
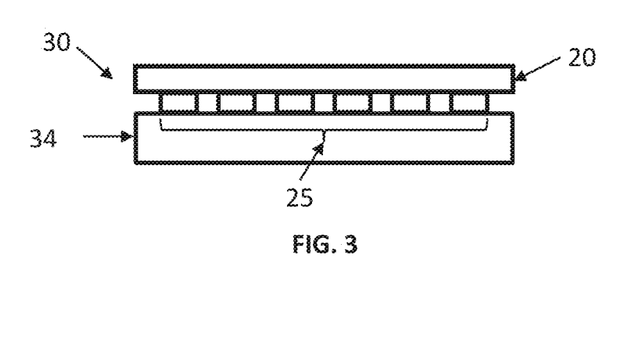
FIG. 3 is schematic diagram of an illustrative light emissive display module.

FIG. 3 is schematic diagram of an illustrative light-emissive display module 30. The light-emissive display module 30 includes a substrate 34, an array of light-emissive elements 25 overlying the substrate 34, a circular polarizer 20 overlying the array of light-emissive elements 25. The circular polarizer 20 is described above. The orientation of the circular polarizer is identical to that described for the OLED display in FIG. 16. The light-emissive elements 25 may be solid-state light sources such as LEDs (light-emitting diodes) or laser diode elements. The light-emissive elements 25 may be micro-LED elements or mini-LED elements. Micro-LEDs are generally LEDs that have light emission dimensions of 50 micrometers by 50 micrometers or less. Mini-LEDs have larger dimensions than micro-LEDs but have light emission dimensions of 1 mm by 1 mm or less. Alternatively, the array of light-emissive elements may be an array of OLED elements. The light-emissive elements 25 are arrayed on a substrate 34. The substrate 34 may be a CMOS circuit substrate having CMOS transistors electrically connected to the light-emissive elements 25. In one Example, the substrate 34 has driver circuitry (not shown in FIG. 3) such that each light-emissive element 25 is individually addressable; in such case, the light-emissive display module 30 is a display where each light-emissive element 25 corresponds to a pixel. The CMOS circuit substrate may be made of a suitable material such as polyimide or silicon.

EXAMPLES

All chemical materials listed herein (and not specifically mentioned by source) are commercially available from Sigma-Aldrich (USA).

Examples of synthesis of four different dichroic dye compounds are shown below.

Blue Dichroic Dye Compound (Structure B)

20 g of Indanthrone was added to a mixture of 40 ml Fuming Sulfuric Acid 20% $SO_3$ and 60 ml Chlorosulfonic Acid, well agitated, heated to 40-55 degrees Celsius and kept at temperature for 3 days. Then the resulted reaction mass was quenched with water and ice, neutralized with 28-30% Ammonium hydroxide and ultrafiltered to remove ammonium sulfate. The retentate was microfiltered and concentrated. Yield 25 g on solid basis. Resulting product was:

(Structure B)

wherein:
X is an ammonium sulfonate, and $1 \leq m \leq 4$;
Z is a Cl (chloro) group, and $0 \leq p \leq 2$; and
$m+p \leq 4$.

Figure 4:
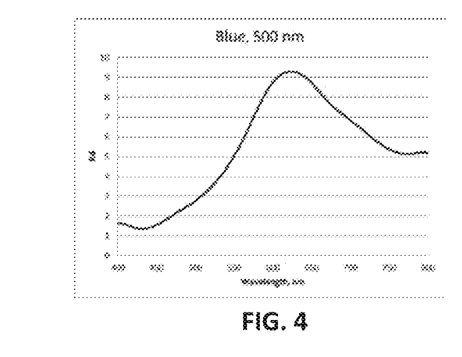
FIG. 4 is a graph of the dichroic ratio verses wavelength for the Blue dichroic dye compound (Structure B) coating on glass in the Example.
Figure 10:
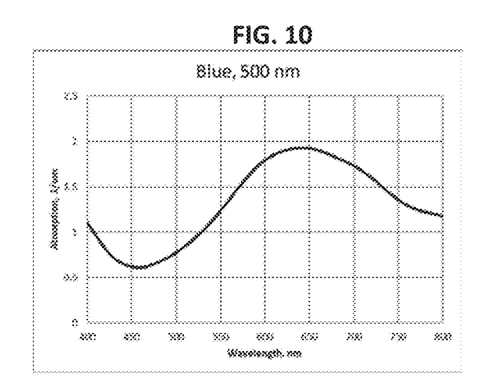
FIG. 10 is a graph of the absorption verses wavelength for the Blue dichroic dye compound (Structure B) coating on glass in the Example.

A lyotropic liquid crystal solution in water of the Blue dichroic dye compound (Structure B) was prepared and shear-coated and dried on a glass substrate. Transmittance spectra were taken for two orientations of the sample (shear-coating direction perpendicular ($T_{per}$) and parallel ($T_{par}$) to the direction of the polarized light incident on the sample). The Dichroic ratio (Kd) was calculated as $\ln(T_{per})/\ln(T_{par})$. FIG. 4 is a graph of the dichroic ratio (Kd) verses wavelength for this Blue dichroic dye compound (Structure B) coating. Maximum Kd occurs around 625 nm and is about 9. FIG. 10 is a graph of the absorption verses wavelength for the Blue dichroic dye compound (Structure B) coating on glass, calculated as ln(total transmittance)/thickness of coating.

Red Dichroic Dye Compound (Structure R)

150 g of pure starting material was prepared by crystallization of commercially available Vat Red 15 from concentrated Sulfuric acid. This material was mixed with 450 ml of Fuming Sulfuric Acid 20% $SO_3$, heated to 36-46 degrees Celsius and kept at temperature for 3 hrs. The reaction mass was quenched with water and Ammonium Hydroxide, the resulted precipitate was isolated, dissolved in water and ultrafiltered. The retentate was microfiltered and concentrated. Yield 180 g on solid basis. Resulting product was:

(Structure R)

and a trans-isomer of structure R, wherein, X is an ammonium sulfonate.

Figure 5:
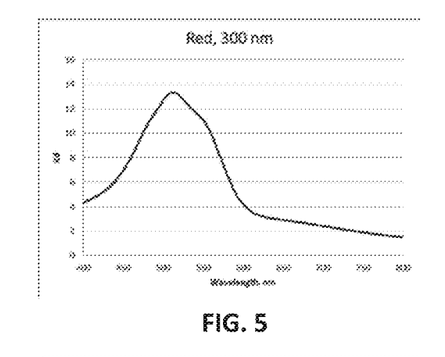
FIG. 5 is a graph of the dichroic ratio verses wavelength for the Red dichroic dye compound (Structure R and trans-isomer of Structure R) coating on glass in the Example.
Figure 11:
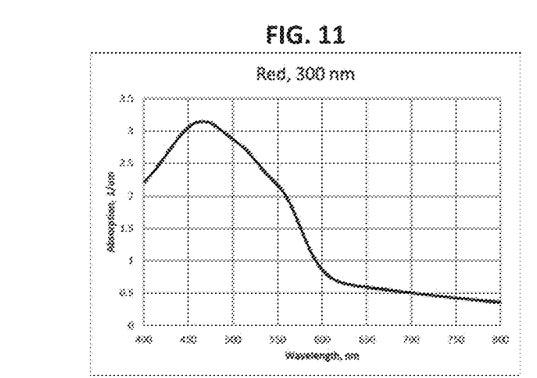
FIG. 11 is a graph of the absorption verses wavelength for the Red dichroic dye compound (Structure R and its trans-isomer) coating on glass in the Example.

A lyotropic liquid crystal solution in water of the Red dichroic dye compound (Structure R and its trans-isomer) was prepared and shear-coated and dried on a glass substrate. Transmittance spectra were taken for two orientations of the sample (shear-coating direction perpendicular ($T_{per}$) and parallel ($T_{par}$) to the direction of the polarized light incident on the sample). The Dichroic ratio (Kd) was calculated as $\ln(T_{per})/\ln(T_{par})$. FIG. 5 is a graph of the dichroic ratio (Kd) verses wavelength for this Red dichroic dye compound (Structure R) coating. Maximum Kd occurs at around 510 nm and is about 13. FIG. 11 is a graph of the absorption verses wavelength for the Red dichroic dye compound (Structure R and trans-isomer of Structure R) coating on glass, calculated as ln(total transmittance)/thickness of coating.

Yellow Dichroic Dye Compound (Structure Y)

2 g of Vat Orange 9 was added to a mixture of 2 ml of Fuming Sulfuric Acid 20% $SO_3$ and 4 ml of Chlorosulfonic Acid, well agitated, heated to 70-90 degrees Celsius and kept at temperature for 30 hours. The reaction mass was quenched with 95% Sulfuric acid and water, neutralized with Ammonium Hydroxide and ultrafiltered to remove inorganic salts. The retentate was microfiltered and concentrated. Yield 2.2 g on solid basis. Resulting product was:

(Structure Y)

wherein:
X is an ammonium sulfonate, and 1≤m≤4;
Z is a Cl (chloro) group, and 0≤p≤2;
and m+p≤6.

Figure 6:
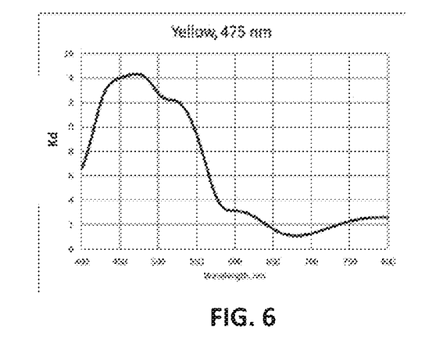
FIG. 6 is a graph of the dichroic ratio verses wavelength for the Yellow dichroic dye compound (Structure Y) coating on glass in the Example.
Figure 12:
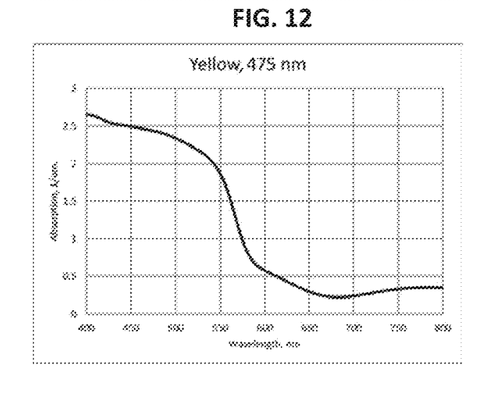
FIG. 12 is a graph of the absorption verses wavelength for the Yellow dichroic dye compound (Structure Y) coating on glass in the Example.

A lyotropic liquid crystal solution in water of the Yellow dichroic dye compound (Structure Y) was prepared and shear-coated and dried on a glass substrate. Transmittance spectra were taken for two orientations of the sample (shear-coating direction perpendicular ($T_{per}$) and parallel ($T_{par}$) to the direction of the polarized light incident on the sample). The Dichroic ratio (Kd) was calculated as $\ln(T_{per})/\ln(T_{par})$. FIG. 6 is a graph of the dichroic ratio (Kd) verses wavelength for this Yellow dichroic dye compound (Structure Y) coating. Maximum Kd occurs at around 450 nm and is about 14. FIG. 12 is a graph of the absorption verses wavelength for the Yellow dichroic dye compound (Structure Y) coating on glass, calculated as ln(total transmittance)/thickness of coating.

Violet Dichroic Dye Compound (Structure Vc)

3.25 g of Isoviolanthrone (TCI America) was mixed with 36 ml Fuming Sulfuric Acid 30% $SO_3$ and agitated overnight. Then the reaction mass was fortified by addition of 47 ml Fuming Sulfuric Acid 65% SO3 and heated to 75-80 degrees Celsius. The reaction time at temperature was 7 hrs. Then the reaction mass was quenched with water, neutralized with Ammonium Hydroxide and ultrafiltered to remove inorganic salts. The retentate was microfiltered and concentrated. Yield 1.7 g on solid basis. Resulting product was:

(Structure Vc)

wherein:
X is an ammonium sulfonate, and 1≤m≤4;
Y is a S(=O)$_2$ (sulfone) group, and 0≤n≤2;
Z is a OH (hydroxy) group, and 0≤p≤4;
R is an O (oxo) group, and 0≤q≤4; and
m+p+q≤6.

Violet Dichroic Dye Compound (Structure Va)

2 g of Pigment Black (BASF) was mixed with 8 ml Fuming Sulfuric Acid 30% $SO_3$ and agitated overnight. Then the acid was fortified by addition of 6 ml Fuming Sulfuric Acid 65% $SO_3$ and heated to 61-65 degrees Celsius. The reaction time at temperature was 8 hrs. Then the reaction mass was quenched with water, neutralized with Ammonium Hydroxide and ultrafiltered to remove inorganic salts. The retentate was microfiltered and concentrated. Yield 2.2 g on solid basis. Resulting product was:

(Structure Va)

or a cis-isomer of Structure Va, wherein:
X is an ammonium sulfonate, and 1≤m≤4;
Y is a S(=O)$_2$ (sulfone) group, and 0≤n≤2;
Z is a OH (hydroxy) group, and 0≤p≤4;
R is an O (oxo) group, and 0≤p≤4; and
m+p+q≤6.

Figure 7:
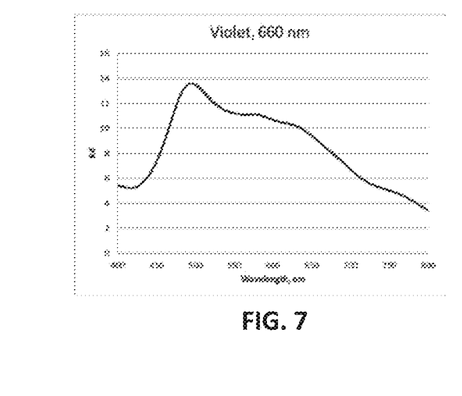
FIG. 7 is a graph of the dichroic ratio verses wavelength for the Violet dichroic dye compound (Structure Va and its cis-isomer) coating on glass in the Example.
Figure 13:
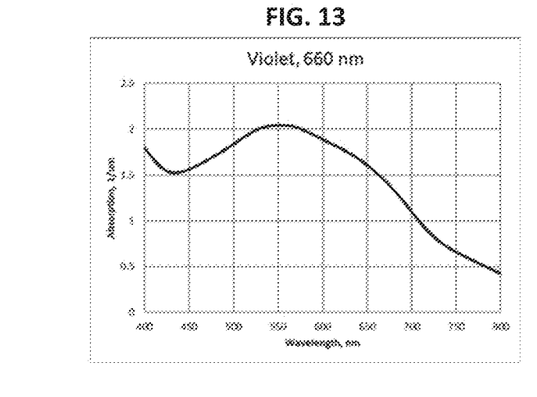
FIG. 13 is a graph of the absorption verses wavelength for the Violet dichroic dye compound (Structure Va and its cis-isomer) coating on glass in the Example.

A lyotropic liquid crystal solution in water of the Violet dichroic dye compound (Structure Va and cis-isomer of Structure Va) was prepared and shear-coated and dried on a glass substrate. Transmittance spectra were taken for two orientations of the sample (shear-coating direction perpendicular ($T_{per}$) and parallel ($T_{par}$) to the direction of the polarized light incident on the sample). The Dichroic ratio (Kd) was calculated as $\ln(T_{per})/\ln(T_{par})$. FIG. 7 is a graph of the dichroic ratio (Kd) verses wavelength for this Violet dichroic dye compound (Structure Va and its cis-isomer) coating. Maximum Kd occurs around 490 nm and is about 14. FIG. 13 is a graph of the absorption verses wavelength for the Violet dichroic dye compound (Structure Va and its cis-isomer) coating on glass, calculated as ln(total transmittance)/thickness of coating.

Example 1

Formulation

Dichroic dye compounds Blue (Structure B), Red (Structure R and trans-isomer of Structure R), Yellow (Structure Y) and Violet (Structure Va and its cis-isomer) are mixed in a certain ratio that defines the spectral performance of the coating. In order to ensure mixing of the components on molecular level the total concentration of the initial mixture is less than 2% solids so that all components are in an isotropic state. For example, in order to prepare 100 mL of the formulation comprising B, Va (including its cis-isomer) and R (including its trans-isomer) components in the solid to solid ratio of 18:7:8 correspondingly targeting 12% solid content one takes 131 mL of the 5% Structure B, 51 mL of the 5% Structure Va (including its cis-isomer), 58 mL of the 5% Structure R (including its trans-isomer) and adds 400 mL of water. Resulting solids concentration is approximately 1.9% by weight.

Then the mixture is filtered through a 0.45 micrometer nylon filter and concentrated to 12% solids by weight using any available method including but not limited to rotary evaporating machines or an ultrafiltration setup.

The final mixture is filtered once again through a 0.45 micrometer nylon filter.

Coating

The Grey Polarizer (GP) coating liquid can be applied to a variety of substrates.

Glass—LCD grade clean glass substrates do not require additional treatment and GP coating liquid can be applied directly to it. One cleaning procedure is as follows. Glass is sonicated in cleaning solution e.g., Alconox cleaner (Alconox Inc.) or similar at 30 degrees Celsius for 30 min. Then soaked in tap water for 15 min followed by the rinsing with deionized water. After that the glass sonicated in water solution of NaOH (10% wt) at 30 degrees Celsius for 30 min. Rinsed again with deionized water and finally dried with compressed air.

TAC—TAC surface is activated via a saponification process in order to ensure uniform wetting and adhesion. TAC film piece is soaked in water for 10 min, then rinsed under water stream. Then the film is placed into water solution of NaOH (6% wt.) at 55 degrees Celsius for 2 min. Thoroughly rinsed with deionized water. Placed on a flat, clean soft cloth and dried with a flow of compressed air. Treated TAC film can be used immediately after this process or later up to 3 days.

COP, PC, PET—Due to low surface energy these plastic substrates require pre-treatment such as a corona or plasma treatment. Adhesion of the coating to the substrates is provided by a primer (MICA A-131-X waterborne primer). The substrate sheet was placed onto a solid flat surface and corona treated a few times at a rate of about 1 cm/s (for a hand-held corona treater BD-20AC, Electro-Technic Products). Immediately after corona treatment the substrate was primed by coating the primer solution at 1% solids using Mayer rod #1.5. Sufficient drying of the primer coated with Mayer rod #1.5 takes place in about 5 seconds under ambient conditions.

TAC and glass substrates can also be primed to make adhesion stronger.

GP Coating

Substrate was pre-treated according to the above examples. Then the substrate was secured onto a solid flat surface. GP formulation of 12% solid content was shear-coated using Mayer rod #4. It takes about 0.5-1 mL to cover an A5 size sheet. The best results are achieved when the GP coating is dried undisturbed under ambient conditions. These coating steps gave approximately 800 nm physical thickness of polarizing plate. For thinner or thicker coatings, a different Mayer rod size can be used.

Testing

Figure 8:
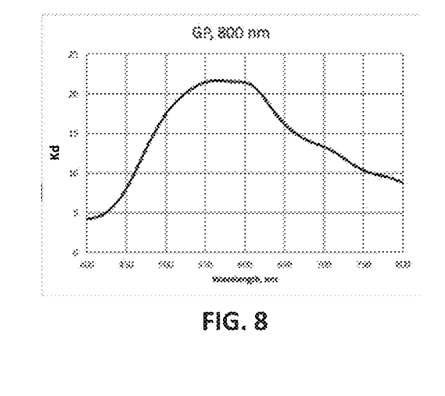
FIG. 8 is a graph of the dichroic ratio verses wavelength for the Grey Polarizer on glass in the Example.

FIG. 8 is a graph of the dichroic ratio verses wavelength for the Grey Polarizer on glass in the Example. Transmittance spectra were taken for two orientations of the sample (shear-coating direction perpendicular ($T_{per}$) and parallel ($T_{par}$) to the direction of the polarized light incident on the sample). The Dichroic ratio (Kd) was calculated as $\ln(T_{per})/\ln(T_{par})$ and graphed at FIG. 8. The grey polarizer has a Kd peak at about 550 nm this peak is a Kd of about 22.

Figure 9:
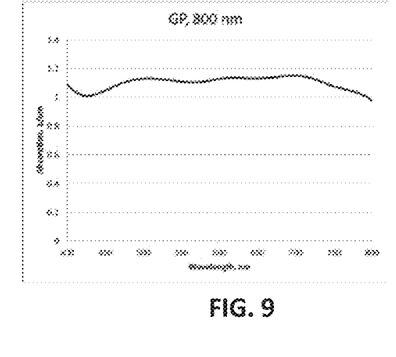
FIG. 9 is a graph of the absorption verses wavelength for the Grey Polarizer on glass in the Example.

FIG. 9 is a graph of the absorption verses wavelength for the Grey Polarizer on glass in the Example, calculated as ln(total transmittance)/thickness of coating. This graph illustrates the uniform absorption spectrum of the Grey Polarizer over the entire visible light wavelength range from 400 to 800 nm.

Thus, embodiments of COATABLE GREY POLARIZER are disclosed.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof. The disclosed embodiments are presented for purposes of illustration and not limitation.

What is claimed is:

1. A linear polarizer, comprising:
   a blue dichroic dye compound, having its maximum visible light absorption in a wavelength range 600 nm-700 nm and a maximum dichroic ratio Kd≤12 in an entire visible wavelength range; and
   a red dichroic dye compound, having its maximum visible light absorption in a wavelength range 430 nm-520 nm and a maximum dichroic ratio Kd≤16 in the entire visible wavelength range;
   wherein the linear polarizer has a dichroic ratio Kd≥18 at 550 nm, and a thickness of the linear polarizer is less than or equal to 2 micrometers.

2. The linear polarizer of claim 1, further comprising:
   a violet dichroic dye compound, having its maximum visible light absorption in a wavelength range 500 nm-620 nm and a maximum dichroic ratio Kd≤16 in the entire visible wavelength range.

3. The linear polarizer of claim 1, further comprising:
a yellow dichroic dye compound, having its maximum visible light absorption in wavelengths≤550 nm and a maximum dichroic ratio Kd≤17 in the entire visible wavelength range.

4. The polarizer of claim 1, wherein the blue dichroic dye compound has a structure B:

(Structure B)

wherein:
X is a SO$_3$H (sulfonic) group or a salt thereof, and 1≤m≤4;
Z is a Cl (chloro) group, and 0≤p≤2; and
m+p≤4.

5. The polarizer of claim 1, wherein the red dichroic dye compound has a structure R:

(Structure R)

or a trans-isomer of structure R, wherein, X is a SO$_3$H (sulfonic) group or a salt thereof.

6. The polarizer of claim 2, wherein the violet dichroic dye compound has a structure Vc:

(Structure Vc)

wherein:
X is a SO$_3$H (sulfonic) group or a salt thereof, and 1≤m≤4;
Y is a S(=O)$_2$ (sulfone) group, and 0≤n≤2;
Z is a OH (hydroxy) group, and 0≤p≤4;
R is an O (oxo) group, and 0≤q≤4; and
m+p+q≤6.

7. The polarizer of claim 2, wherein the violet dichroic dye compound has a structure Va:

(Structure Va)

or a cis-isomer of Structure Va, wherein:
X is a SO$_3$H (sulfonic) group or a salt thereof, and 1≤m≤4;
Y is a S(=O)$_2$ (sulfone) group, and 0≤n≤2;
Z is a OH (hydroxy) group, and 0≤p≤4;
R is an O (oxo) group, and 0≤q≤4; and
m+p+q≤6.

8. The polarizer of claim 3, wherein a yellow dichroic dye compound has a structure Y:

(Structure Y)

wherein:
X is a SO$_3$H (sulfonic) group or a salt thereof, and 1≤m≤4;
Z is a Cl (chloro) group, and 0≤p≤2; and
m+p≤6.

9. A linear polarizer film, comprising:
a substrate;
a linear polarizer according to claim 1 overlying the substrate.

10. The linear polarizer film of claim 9, wherein the substrate is selected from the group consisting of: glass, TAC, PET, PC, COP, OCA film, and anti-reflection film.

11. A pair of eyeglasses comprising a lens, said lens comprising the linear polarizer film of claim 9.

12. A circular polarizer, comprising:
a retarder, configured as an achromatic quarter-wave plate; and
a linear polarizer according to claim 1 overlying the retarder such that the retarder and a first major surface of the linear polarizer are facing toward each other.

13. The circular polarizer of claim 12, additionally comprising an anti-reflection coating or anti-reflection film overlying the linear polarizer such that light initially passing through the anti-reflection coating or anti-reflection film then passes through the linear polarizer before reaching the retarder.

14. An OLED display, comprising:
an OLED display panel;
a circular polarizer according to claim 12 overlying the OLED display panel.

15. A light emissive display module, comprising:
a circuit substrate;
an array of light emissive elements overlying the circuit substrate; and
a circular polarizer according to claim 12 overlying the array of light emissive elements.

16. The light emissive display module of claim 15, wherein the circuit substrate is a CMOS circuit substrate, comprising CMOS transistors electrically connected to the light emissive elements.

17. The light emissive display module of claim 15, wherein the circuit substrate is selected from the group consisting of, silicon and polyimide.

18. The light emissive display module of claim 15, wherein the light emissive elements are solid state light source elements.

19. The light emissive display module of claim 18, wherein the solid-state light source elements are light-emitting diodes (LEDs).

20. The light emissive display module of claim 18, wherein the light emissive elements are mini-LED or micro-LED elements.

\* \* \* \* \*